(12) United States Patent
Howland et al.

(10) Patent No.: US 8,257,278 B2
(45) Date of Patent: Sep. 4, 2012

(54) METAL COMPOSITE GUIDE WIRE

(75) Inventors: Jonathan M. Howland, Temecula, CA (US); Wayne E. Cornish, Fallbrook, CA (US); Mark T. Richardson, Escondido, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2147 days.

(21) Appl. No.: 10/145,840

(22) Filed: May 14, 2002

(65) Prior Publication Data

US 2003/0216668 A1    Nov. 20, 2003

(51) Int. Cl.
   *A61B 5/00*    (2006.01)
   *A61M 25/00*    (2006.01)
(52) U.S. Cl. ..................................................... 600/585
(58) Field of Classification Search .................. 600/585, 600/433–435; 604/264, 530, 523–525, 533–535, 604/103.1; 428/600, 607, 685, 660
   See application file for complete search history.

(56) References Cited

U.S. PATENT DOCUMENTS

| | | | |
|---|---|---|---|
| 4,538,622 A | 9/1985 | Samson et al. | |
| 4,748,986 A | 6/1988 | Morrison et al. | |
| 4,875,489 A | 10/1989 | Messner et al. | |
| 4,955,384 A * | 9/1990 | Taylor et al. | 600/585 |
| 4,966,163 A | 10/1990 | Kraus et al. | |
| 5,061,273 A | 10/1991 | Yock | |
| 5,135,503 A | 8/1992 | Abrams | |
| 5,230,348 A | 7/1993 | Ishibe et al. | |
| 5,341,818 A | 8/1994 | Abrams et al. | |
| 5,345,945 A | 9/1994 | Hodgson et al. | |
| 5,365,943 A * | 11/1994 | Jansen | 600/585 |
| 5,636,641 A | 6/1997 | Fariabi | |
| 6,019,736 A * | 2/2000 | Avellanet et al. | 600/585 |
| 6,200,685 B1 | 3/2001 | Davidson | |
| 6,352,515 B1 | 3/2002 | Anderson et al. | |

FOREIGN PATENT DOCUMENTS

| | | |
|---|---|---|
| EP | 806220 A2 * | 11/1997 |
| WO | WO 01/45787 A1 | 6/2001 |

OTHER PUBLICATIONS

Brown, Robert, Unique Properties Required of Alloys for the Medical and Dental Products Industry, Jul. 1996.*
Boylan, John F., et al.; "Medical Devices Configured From Deep Drawn Nickel-Titanium and Nickel-Titanium Clad Alloys and Method of Making the Same;" U.S. Appl. No. 10/155,910, filed May 24, 2002.

(Continued)

*Primary Examiner* — Brian Szmal
(74) *Attorney, Agent, or Firm* — Fulwider Patton LLP

(57) ABSTRACT

A guide wire for guiding a medical device within a patient is disclosed. The guide wire has a solid inner core made of high modulus material such as Conichrome® or a rhenium alloy, and an outer shell made of a flexible, kink resistant material such as a nickel-titanium alloy. Preferably, the modulus of elasticity of the inner core material is at least about 20 percent greater than that of the outer shell material. The outer shell is mechanically joined to the inner core through a drawing or cladding process. In various embodiments, the distal end of the guide wire can be tapered by grinding away the outer shell to expose the inner core. Because of its stiffness, it can be manually shaped by the physician or cardiologist.

23 Claims, 1 Drawing Sheet

OTHER PUBLICATIONS

Internet Web Site—www.fwmetals.com /spec_sheets/conichrome.htm (Fort Wayne Metals/Research Products Corp.); Conichrome®, 2 pgs., visited Apr. 9, 2002.

Internet Web Site—www.fwmetals.com/spec_sheets/nitinol.htm (Fort Wayne Metals/Research Products Corp.); Nitinol, 2 pgs., visited Apr. 9, 2002.

Internet Web Site—www.fwmetals.com/spec_sheets/dft.htm (Fort Wayne Metals/Research products Corp.); DFT® Wire, 2 pgs., visited Apr. 9, 2002.

Schaffer, Jeremy E., "General Characteristics of DFT® Composite Wire", Brochure from Fort Wayne Metals Research Products Corporation; 11 pgs., Feb. 6, 2002.

* cited by examiner

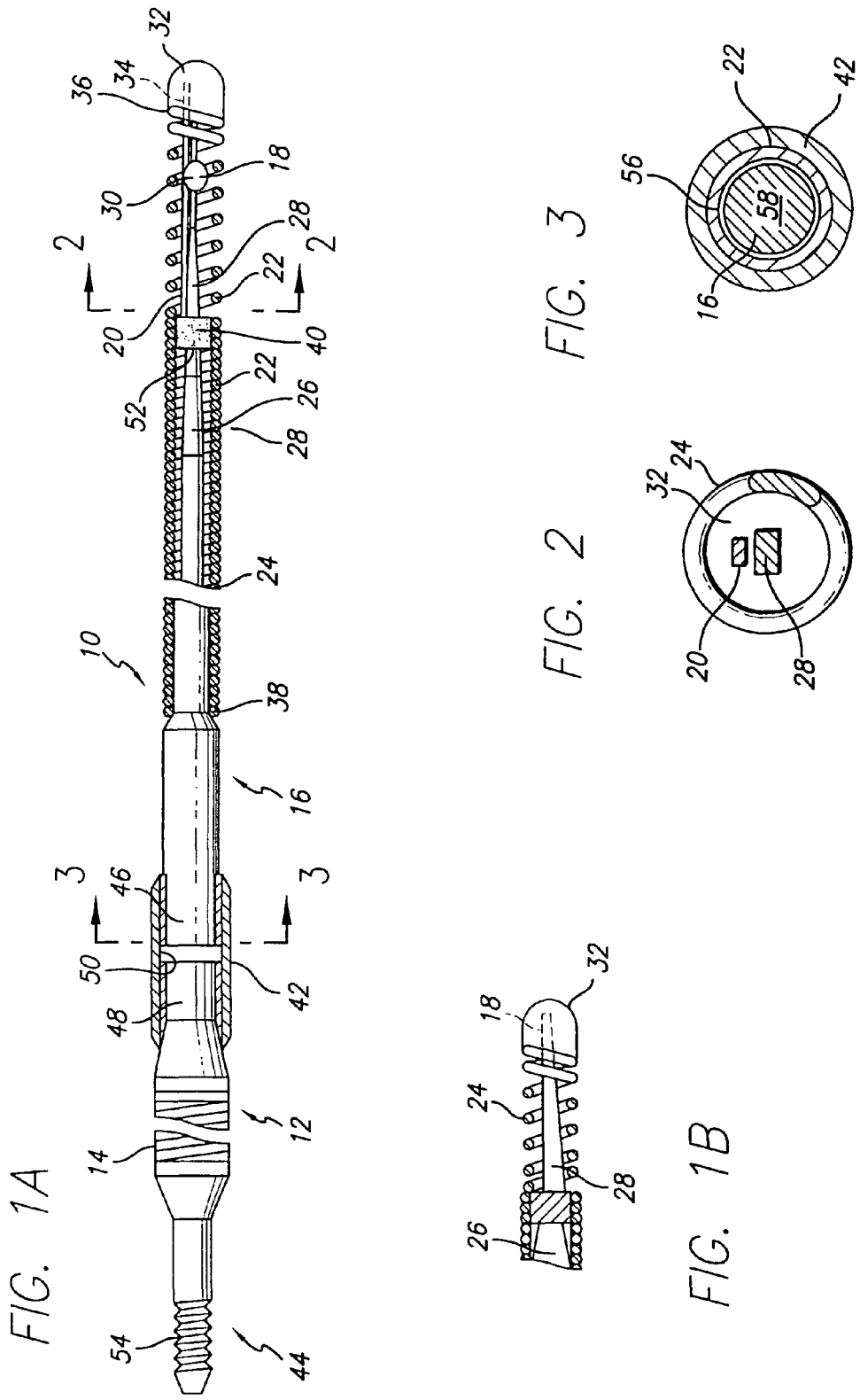

METAL COMPOSITE GUIDE WIRE

BACKGROUND OF THE INVENTION

The present invention relates to the field of advanced medical devices and particularly to intracorporeal devices for performing or aiding in the performance of therapeutic or diagnostic procedures. The intracorporeal devices may be guiding members such as guide wires for advancing intraluminal devices within various body lumens. The intracorporeal medical devices include stent delivery catheters, balloon dilatation catheters, atherectomy catheters, electrophysiology catheters and the like.

In a typical percutaneous coronary procedure, a guiding catheter having a pre-formed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guide wire is first advanced by itself through the guiding catheter until the distal tip of the guide wire extends beyond the arterial location where the procedure is to be performed. Then a rapid exchange type catheter, such as described in U.S. Pat. No. 5,061,273 (Yock) whose contents are hereby incorporated by reference, is mounted onto the proximal portion of the guide wire which extends out of the proximal end of the guiding catheter outside of the patient. The catheter is advanced over the guide wire, while the position of the guide wire is fixed, until the operative element on the rapid exchange type catheter is disposed within the arterial location where the procedure is to be performed. After the procedure is performed, the rapid exchange type catheter may be withdrawn from the patient over the guide wire, or the guide wire may be repositioned within the coronary anatomy for an additional procedure. Of course, the procedure may also be performed with an over-the-wire (OTW) type catheter and is not limited to just rapid exchange (RX) type catheters.

A guide wire may also be used in conjunction with the delivery of an intravascular stent. One method and system involves disposing a compressed or otherwise small diameter stent over an expandable member, such as a balloon, at the distal end of a catheter. The physician advances the catheter through the patient's vascular system over a guide wire until the stent is at the desired location within a blood vessel. The expandable member on the catheter is inflated to expand the stent within the blood vessel. The dilated expandable member is then deflated and the catheter withdrawn, leaving the expanded stent within the blood vessel. Once deployed, the expandable member ensures patency of the blood vessel by holding the passageway open. This latter method and system can be used concurrently with balloon angioplasty or subsequent thereto.

Further details of guide wires and devices associated therewith for various interventional procedures can be found in, for example, U.S. Pat. No. 4,748,986 (Morrison et al.); U.S. Pat. No. 4,538,622 (Samson et al.); U.S. Pat. No. 5,135,503 (Abrams); U.S. Pat. No. 5,341,818 (Abrams et al.); and U.S. Pat. No. 5,345,945 (Hodgson, et al.), whose contents are hereby incorporated by reference.

Conventional guide wires for angioplasty, stent delivery, atherectomy, and other intravascular procedures usually have an elongate core with one or more segments near the distal end thereof that taper distally to smaller cross-sections. A flexible body, such as a helical coil or a tubular body of polymeric material, is typically disposed about and secured to at least part of the distal portion of the core. A shapeable tip, which may be the distal extremity of the core or a separate shapeable ribbon that is secured to the distal extremity of the core, extends through the flexible body and is secured to the distal end of the flexible body by soldering, brazing, or welding; or by use of an adhesive in the case of a polymeric flexible body which forms a rounded distal tip or tip ball. This rounded, distal or leading tip is highly flexible so that it does not damage or perforate the vessel. The portion behind the distal tip is increasingly stiff to better support a balloon catheter or similar device.

The shapeable member or ribbon of a typical guide wire is a small diameter wire that has been flattened to a relatively constant transverse profile. Flattening of the shapeable member facilitates the shapeability of the member. However, a shapeable member having a constant transverse profile or flexibility could be subject to prolapse during use. Prolapse occurs when the shapeable member gets bent back on itself inside a constrained lumen, and is difficult to straighten out with only proximal manipulation.

Some guide wires have been formed from a pseudoelastic, shape memory alloy such as nitinol (i.e., nickel-titanium or NiTi) to achieve both flexibility and strength. When stress is applied to nitinol alloy exhibiting pseudoelastic characteristics at a temperature at or above the transformation of martensite to austenite is complete, the material deforms elastically until it reaches a particular stress level where the alloy then undergoes stress-induced phase transformation from austenite back to martensite. As the phase transformation proceeds, the alloy undergoes significant increases in strain but with little or no corresponding increases in applied stress. In other words, the strain increases while the stress applied remains essentially constant until the transformation of the austenite to the martensite is complete. The martensite that appears under this type of loading is commonly called stress induced martensite (SIM). Thereafter, further increases in stress are necessary to cause more deformation in the material.

If the load on the nitinol alloy is removed before any permanent deformation has occurred, the martensite in the material elastically recovers and transforms back to austenite. The gradual reduction in stress first causes a decrease in strain. As stress reduction reaches the level at which the martensite transforms back to the austenite, the stress level in the material remains again essentially constant until the transformation back to austenite is complete. That is, there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as pseudoelasticity. These properties to a large degree allow a guide wire core of a pseudoelastic material to have both flexibility and strength. The term "pseudoelasticity" is sometimes used interchangeably with "superelasticity."

While the properties of the guide wires formed from pseudoelastic or superelastic material were very advantageous, it was found that some of the guide wires and guiding members formed from such materials did not have optimal push and torque transmission characteristics.

SUMMARY OF THE INVENTION

The present invention in one embodiment is directed to an intravascular guide wire comprising a wire core having a distal end and a proximal end, wherein the wire core includes an inner core made of a first material at least partially covered by an outer shell made of a second material. The first material preferably has a modulus of elasticity that is at least about 20 percent greater than a modulus of elasticity of the second material. Alternatively, the modulus of elasticity of the first material is preferably at least about $15 \times 10^6$ psi greater than the modulus of elasticity of the second material.

Structurally, the guide wire also has a coil disposed at the distal end of the wire core, and a ball tip disposed at the distal end of the wire core. In addition, the intravascular guide wire of the present invention has preferably a distal end that is tapered. Through a grinding process, the taper is created by removing material to gradually reduce the thickness of the outer shell distally, eventually exposing the inner core. The taper may continue distally to also shape the inner core. The present invention intravascular guide wire optionally includes a stainless steel proximal portion located proximal to the covered inner core. Also, the wire core may optionally be at least partially covered by one or more polymer coatings.

In various embodiments, the first material includes an alloy selected from the group consisting of cobalt-chromium-tungsten-nickel-iron (known in the art as L605), nickel-cobalt-chromium-molybdenum (known commercially as MP35N), cobalt-chromium-nickel-molybdenum-iron (known commercially as Conichrome®), molybdenum-rhenium, or tungsten-rhenium. The second material includes an alloy selected from the group consisting of nickel-titanium, nickel-titanium-vanadium, nickel-titanium-niobium, nickel-titanium-chromium, nickel-titanium-palladium, nickel-titanium-platinum, or nickel-titanium-tantalum.

The first material is mechanically clad, bonded or joined to the second material through a compressive force. This is typically accomplished through a drawing process in which the outer shell is drawn over the solid inner core. In one core-to-tip guide wire embodiment, the same materials in the outer shell and the inner core extend continuously from the proximal end to the distal end.

According to the present invention, the flexible metal clad outer shell with a stiffer inner core guide wire eases processing as compared to a monofilament nitinol core that is then alloyed or chemically processed to change its properties. Some advantages of the present invention are control of the exact composition of the materials in the outer shell and inner core, and precise control of the thickness of the material in the outer shell versus the inner core. In a chemically alloyed or heat treated nitinol core, such control of the influence of impurities in the material and thicknesses of the outer shell are more challenging.

With the aforementioned combination of outer shell and inner core materials, the guide wire benefits from the qualities of both. More precisely, the high modulus inner core is much stiffer in bending than the outer shell. Thus, the overall diameter of the guide wire (i.e., crossing profile) is maintained yet the wire is much stiffer due to the presence of the high modulus inner core. So for a given small crossing profile, the present invention guide wire provides improved stiffness for better pushability, device support, and efficient torque transmission from the proximal end to the distal end.

Moreover, since the outer shell is preferably made of a nickel-titanium alloy (i.e., nitinol), the present invention guide wire remains highly flexible yet resists kinking, which are two important features of nitinol alloys. Since much of the guide wire is covered in nitinol or similar outer shell, biocompability issues with the selected inner core materials are minimized.

In one embodiment, the nitinol outer shell has an outside diameter of about 0.008 to 0.0035 inch. Given these outside shell diameters, an outside diameter of an inner core of Conichrome® or a rhenium alloy is preferably about 15 to 40 percent of the outside diameter of the outer shell. These sizes appear empirically to provide an acceptable balance between the stiffness of the inner core versus the flexibility and kink resistance of the outer shell.

Given inner core and outer shell construction of the present invention, the distal end can be tapered through a material removal process to gradually taper the outer shell until it is completely removed thus exposing the stiff inner core. The stiff inner core may itself be machined or formed until a specific profile is achieved. A benefit of this processing is that the exposed stiff inner core can be manually shaped or bent by the cardiologist or physician. This eliminates the need for a separate shaping ribbon. Without a shaping ribbon, the construction of the guide wire is simplified, the material compatibility and assembly of the shaping ribbon to the distal end of the guide wire problems disappear, and the costs for the device are reduced.

These and other advantages of the invention will become more apparent from the following detailed description of the invention when taken in conjunction with the accompanying exemplary drawings.

BRIEF DESCRIPTION OF THE DRAWINGS

FIG. 1(a) is a side elevational view, shown partially in cross-section, of a guide wire embodying features of the present invention.

FIG. 1(b) is a partial view of the distal end of the present invention guide wire having a core-to-tip configuration.

FIG. 2 is a cross-sectional view of the guide wire shown in FIG. 1(a) taken along line 2-2.

FIG. 3 is a cross-sectional view of the guide wire shown in FIG. 1(a) taken along line 3-3.

DETAILED DESCRIPTION OF THE PREFERRED EMBODIMENTS

The present invention in an exemplary embodiment is directed to a guide wire having a flexible outer shell made of one material mechanically joined to a stiff inner core made of another material. The guide wire thus benefits from the properties of both materials.

FIG. 1(a) illustrates one embodiment of the present invention guide wire 10 that includes an elongated wire core 12 with a proximal core section 14 and a distal core section 16. At the distal end 18 of the distal core section 16 are an optional shapeable member 20, and a flexible body, which in this embodiment are one or more helical coils 22, 24. Preferably, the helical coils 22, 24 are disposed about and secured to the distal core section 16. More precisely, the coils 22, 24 are attached to the wire core at a proximal location 38 and an intermediate location 40 by a suitable solder or weld. Preferably, the distal section of the distal helical coil 24 is made of a radiopaque metal such as platinum, platinum-nickel, iridium, or tantalum alloys to facilitate the observation thereof by fluoroscopy while inside a patient's body. The most distal section of the helical coil 24 may stretch anywhere from 0 to about 30 percent of its length.

The distal core section 16 has an optional tapered segment 26 and an optional flexible core segment 28 which is distally contiguous to the tapered segment 26. At the very distal end of the flexible core segment 28 is a rounded distal extremity 30. Of course, the rounded distal extremity 30 may be of other shapes and sizes, can be flattened, or omitted altogether. It is commonly made of solder material. Such a bulbous structure is useful in preventing the sharp distal end 18 of the flexible core segment 28 from unexpectedly passing through the spacings between the turns of the stretched out helical coil 24.

In an alternative embodiment core-to-tip design, shown in FIG. 1(*b*), the flexible core segment 28 extends continuously to engage a rounded tip ball 32 at the very distal end of the guide wire 10. In this embodiment, the rounded distal extremity 30 and the shapable member 20 are omitted. The extended flexible core segment 28 is deformable and now serves as a shapeable member.

Back in FIG. 1(*a*), the optional shapeable member or shaping ribbon 20 extends distally and engages the rounded tip ball at distal end 34. Typically, the rounded tip ball 32 is formed by solder or weld and joins the distal end of the coil 36 to the distal end 34 of the shapeable member 20. Toward the opposite end, the shapeable member 20 is connected to the distal core section 16 via the solder or weld at intermediate location 40. Further proximally, the proximal end 52 of the shapeable member 20 preferably extends by up to 2.5 cm beyond the intermediate location 40.

Toward the proximal end 44 of the wire core 12 is the proximal core section 14, made of a relatively high strength material such as stainless steel. In the embodiment depicted in FIG. 1(*a*), the proximal core section 14 is joined to the more flexible distal core section 16 by a connector element 42. In a core-to-tip alternative embodiment shown in FIG. 1(*b*), as the name suggests, the material comprising the distal core section 16 extends from the distal end 18 continuously to the proximal end 44. As such, the connector element 42 is omitted and the high strength material for the proximal section is not used. In yet another alternative embodiment, the distal core section 16 of FIG. 1(*b*) is joined using the connector element 42 to the proximal core section 14 as shown in FIG. 1(*a*).

As mentioned earlier, the connector element 42, preferably made of a superelastic alloy such as nitinol, connects the proximal end 46 of the distal core section 16 to the distal end 48 of the proximal core section 14. Hence, the connector element 42 must be able to transmit torque efficiently between the two sections 14, 16. As seen in FIG. 1(*a*), the connector element 42 is tubular shaped with an inner lumen 50 that receives the proximal end 46 and the distal end 48. Both ends 46, 48 may be pressed fit into the connector element 42 or they may be secured therein by crimping, swaging, welding, brazing, soldering, or adhesive bonding.

Also at the proximal end 44 is an optional docking extension 54. The docking extension 54 enables a guide wire to be made in discrete sections that can be separated or joined by use of threaded or other mating components. The mating components enable over-the-wire type catheters to be exchanged over a short wire of, for example, 190 cm or less. Examples of docking extensions are shown in, for example, U.S. Pat. Nos. 4,966,163 (Kraus et al.) and U.S. Pat. No. 4,875,489 (Messner et al.) whose contents are hereby incorporated by reference. Without the detachable sections, the guide wire for an over-the-wire catheter would typically extend to 300 cm.

FIGS. 2-3 are cross-sectional views of the guide wire 10 taken along lines 2-2 and 3-3, respectively. At the distal end 18 of the flexible core segment 28, FIG. 2 shows a cross-section of the flexible core segment 28, the shapeable member 20, the helical coil 24, and the proximal side of the tip ball 32.

An optional lubricious coating 25 made from polysiloxane, for example, may partially or fully cover the wire core 12. It extends preferably at least the length of the proximal core section 14. The lubricious coating may be a fluoropolymer such as TEFLON® available from Du Pont. The distal core section 16 may also be partially or fully covered in a lubricious coating, known in the art as a MICROGLIDE™ coating. Hydrophilic coatings may also be employed on both the proximal and distal core sections of the guide wire.

In various embodiments of the present invention guide wire, the wire core 12 may be formed from stainless steel, nitinol or NiTi alloys, or combinations thereof such as described in U.S. Pat. No. 5,341,818 (Abrams et al.), whose contents are incorporated herein by reference. Other materials such as the high strength alloys described in U.S. Pat. No. 5,636,641 (Fariabi), which is incorporated herein by reference, may also be used.

In one embodiment, the guide wire 10 has a wire core 12 that is made from an inner core 58 of a first material and an outer shell 56 of a second material wherein the first material of the inner core is relatively stiffer than the outer shell material. FIG. 3 provides a cross-sectional view taken along line 3-3 of FIG. 1(*a*) showing such a structure. In particular, FIG. 3 illustrates a cross-section of the distal core section 16 with an outer shell 56 covering an inner core 58.

In the core-to-tip embodiment of FIG. 1(*b*), the composition of the stiff inner core 58 inside a more flexible outer shell 56 preferably extends from a proximal end 44 of the wire core 12 continuously to the distal end 18. The stainless steel proximal core section 14 can optionally be omitted in such an embodiment. In another embodiment described earlier, the stiff inner core 58 inside a more flexible outer shell 56 are contained in the distal core section 16 as shown in FIG. 1(*b*), which is joined by the connector element 42 to the proximal core section 14 shown in FIG. 1(*a*).

In the present exemplary embodiment, the stiffer inner core material has a modulus of elasticity that is at least about 20 percent greater than a modulus of elasticity of the more flexible outer shell material. In another embodiment, the modulus of elasticity of the inner core material is at least about $15 \times 10^6$ psi greater than the modulus of elasticity of the outer shell material. Based on empirical observation, the given strength differences between the outer shell and the inner core provide sufficient pushability and torque transmission improvements yet do not detract appreciably from the flexibility and kink resistance of the guide wire.

In various embodiments, the outer shell material is an alloy such as, for example, nickel-titanium, nickel-titanium-vanadium, nickel-titanium-niobium, nickel-titanium-chromium, nickel-titanium-palladium, nickel-titanium-platinum, or nickel-titanium-tantalum. Further details of an outer shell 56 made from nitinol can be found in, for example, U.S. Pat. No. 6,352,515 (Anderson et al.) and U.S. Pat. No. 5,341,818 (Abrams et al.), whose contents are hereby incorporated by reference.

The more rigid materials used in the inner core 58 include alloys such as cobalt-chromium-tungsten-nickel-iron (L605), nickel-cobalt-chromium-molybdenum (MP35N), cobalt-chromium-nickel-molybdenum-iron (Conichrome®), molybdenum-rhenium, or tungsten-rhenium. In one embodiment with a nitinol outer shell 56 and a Conichrome® of rhenium alloy inner core 58, the outside diameter of the outer shell is about 0.008 to 0.0035 inch and an outside diameter of the inner core 58 is about 15 to 40 percent of the outside diameter of the outer shell 56. In the alloys listed above and elsewhere, the alloys might contain traces of other elements or impurities not expressly identified.

As for the stiffer inner core 58, in one embodiment, the material includes about 50 to 60 percent molybdenum and a remaining balance of rhenium. In another embodiment, the material for the stiffer inner core 58 is made from about 2 to 26 percent rhenium and a remaining balance of tungsten. Through empirical observations, these compositions appear to provide an acceptable balance between guide wire flexibility and strength. The alloy compositions are given in terms of atomic percent.

The flexible outer shell 56 is joined to the stiffer inner core 58 through a mechanical joining process. This essentially metal cladding process is accomplished in multiple stages of cold drawing through a series of dies; the tubular shaped outer shell 56 is joined to the solid inner core 58 by undergoing a series of compressive and tensile loads.

As seen in FIGS. 1(*a*) and 1(*b*), the distal core section 16 has a tapered segment 26 as does the flexible core segment 28. These multiple tapers are ground through various techniques known in the art. Through these grinding processes, the thickness of the outer shell 56 shown in FIG. 3 is gradually diminished until the inner core 58 is exposed. Such an embodiment is illustrated in FIG. 1(*a*). The exposed inner core 58 is deformable and acts as a shapeable member. Thus, the need for a separate shapeable member 20 is eliminated.

Furthermore, by use of a flexible outer shell 56 made of a material such as nitinol and a more rigid inner core 58 made of a material such as Conichrome® or a rhenium alloy, the present invention guide wire 10 benefits from the physical properties of both materials. That is, the nitinol outer shell maintains a kink resistant nature of the distal core section 16 while the more rigid inner core 58 improves pushability and increases torque transmission efficiency. Moreover, the greater strength of the inner core 58 provides better support for any device used in conjunction with the present invention guide wire 10.

The overall length and diameter of guide wire 10 may be varied to suit the particular procedures in which it is to be used and is dependent on the materials from which it is constructed. Generally, the length of the guide wire 10 ranges from about 65 cm to about 320 cm, and more typically ranging from about 160 cm to about 200 cm.

Commercially available guide wires for coronary anatomy typically have lengths of about 175 cm or about 190 cm. Guide wire diameters generally range from about 0.008 inch to about 0.035 inch (0.2 to 0.9 mm), and more typically range from about 0.01 inch to about 0.018 inch (0.25 to 0.55 mm). Commercially available guide wires for coronary use typically have diameters of about 0.01, 0.012 and 0.014 inch (0.25, 0.3 and 0.036 mm, respectively).

In various embodiments, the helical coils 22, 24 are made from wire with a cross-sectional diameter of about 0.001 to about 0.004 inch (0.025-0.1 mm), and preferably about 0.002 to about 0.003 inch (0.05-0.008 mm). Multiple turns of the distal portion of helical coils 22,24 may be expanded to provide additional flexibility. The helical coils 22, 24 may further have a diameter or transverse dimension that is about the same as the proximal core section 14. One or more of the helical coils 22, 24 may individually or together have a length of about 2 cm to about 40 cm or more, and preferably about 2 cm to about 10 cm in length. Furthermore, the helical coils 22, 24 may at least in part be formed of a suitable radiopaque material such as platinum, palladium, or alloys thereof, or formed of other materials such as stainless steel and coated with a radiopaque material such as gold. In an alternative embodiment, the helical coils 22, 24 may instead be replaced by a sleeve formed from a polymeric material such as polyamide, polyethylene, polyurethane, TFE, PTFE, ePTFE and other similar materials.

While the present invention has been described and illustrated in terms of its use as an intravascular guide wire, it will be apparent to those skilled in the art that the present invention can be applied to other medical devices. Moreover, modifications and improvements may be made to the above-described exemplary embodiments without departing from the scope of the invention.

What is claimed is:

1. An intravascular guide wire, comprising:
   a wire core having a distal end and a proximal end, wherein the wire core includes an inner core made of a first material that is a rhenium alloy at least partially covered by an outer shell made of a second material that is a nickel-titanium alloy;
   a stainless steel proximal portion attached to the proximal end of the wire core;
   a taper at the distal end of the wire core;
   a coil disposed at the distal end of the wire core; and
   a distal tip disposed at the distal end of the wire core.

2. The intravascular guide wire of claim 1, wherein the wire core is more flexible than the stainless steel proximal portion.

3. The intravascular guide wire of claim 1, wherein the second material includes an alloy selected from the group consisting of nickel-titanium, nickel-titanium-vanadium, nickel-titanium-niobium, nickel-titanium-chromium, nickel-titanium-palladium, nickel-titanium-platinum, or nickel-titanium-tantalum.

4. The intravascular guide wire of claim 1, wherein the taper includes a gradual reduction in a thickness of the outer shell to ultimately expose the inner core.

5. The intravascular guide wire of claim 1, wherein a modulus of elasticity of the first material is at least about $15 \times 10^6$ psi greater than the modulus of elasticity of the second material.

6. The intravascular guide wire of claim 1, wherein an outside diameter of the inner core is about 15 to 40 percent of an outside diameter of the outer shell.

7. The intravascular guide wire of claim 1, wherein the first material is mechanically joined to the second material through a compressive force.

8. The intravascular guide wire of claim 1, wherein the outer shell has an outside diameter of about 0.008 to 0.0035 inch, and wherein an outside diameter of the inner core is about 15 to 40 percent of the outside diameter of the outer shell.

9. The intravascular guide wire of claim 1, wherein the rhenium alloy is tungsten-rhenium.

10. An intravascular guide wire, comprising:
    a wire core having a distal end and a proximal end, wherein the wire core includes an inner core made of a first material that is a rhenium alloy at least partially covered by and mechanically joined to an outer shell made of a second material that is a nickel-titanium alloy;
    a stainless steel proximal portion attached to the proximal end of the wire core;
    a taper at the distal end of the wire core, wherein the taper includes a portion of the inner core not covered by the outer shell and a portion covered by the outer shell;
    a coil disposed at the distal end of the wire core;
    a distal tip disposed at the distal end of the wire core; and
    a polymer coating at least partially covering the wire core.

11. The intravascular guide wire of claim 10, wherein the outer shell is clad to the inner core.

12. The intravascular guide wire of claim 10, wherein the second material includes an alloy selected from the group consisting of nickel-titanium, nickel-titanium-vanadium, nickel-titanium-niobium, nickel-titanium-chromium, nickel-titanium-palladium, nickel-titanium-platinum, or nickel-titanium-tantalum.

13. The intravascular guide wire of claim 10, wherein the first material includes about 50 to 60 percent molybdenum and a remaining balance of rhenium.

14. The intravascular guide wire of claim 10, wherein the first material and the second material extend continuously from the tapered distal end of the wire core to the proximal end thereof.

15. The intravascular guide wire of claim 10, wherein the rhenium alloy is tungsten-rhenium.

16. The intravascular guide wire of claim 10, wherein the wire core has greater flexibility than the stainless steel proximal core portion.

17. A method for providing an intravascular guide wire, comprising:
    providing a wire core having a distal end and a proximal end, and including
    an inner core made of a first material that is a rhenium alloy;
    an outer shell made of a second material that is a nickel-titanium alloy that at least partially covers the inner core;
    compressing the inner core and the outer shell together to create a mechanical bond therebetween;
    wherein the first material has a modulus of elasticity that is at least about 20 percent greater than a modulus of elasticity of the second material;
    attaching a stainless steel proximal core portion to the proximal end of the wire core;
    disposing a coil at the distal end of the wire core; and
    disposing a ball tip at the distal end of the wire core.

18. The method of claim 17, wherein compressing the inner core and the outer shell together includes drawing the outer shell over the inner core.

19. The method of claim 17, wherein the second material includes an alloy selected from the group consisting of nickel-titanium, nickel-titanium-vanadium, nickel-titanium-niobium, nickel-titanium-chromium, nickel-titanium-palladium, nickel-titanium-platinum, or nickel-titanium-tantalum.

20. The method of claim 17, wherein the method further comprises at least partially covering the outer shell with a polymer coating.

21. The method of claim 17, wherein the method further comprises grinding the distal end of the wire core to create a tapered profile.

22. The method of claim 17, wherein the method further comprises grinding a distal end of the outer shell creating a gradual taper that exposes the inner core.

23. The method of claim 17, wherein the wire core has greater flexibility than the stainless steel proximal core portion.

\* \* \* \* \*